United States Patent [19]
Nielsen et al.

[11] Patent Number: 5,498,816
[45] Date of Patent: Mar. 12, 1996

[54] PROCESS FOR THE DEHYDROGENATION OF HYDROCARBONS

[75] Inventors: Poul E. H. Nielsen, Fredensborg; Peter Lehrmann, Birkerod, both of Denmark

[73] Assignee: Haldor Topsøe A/S, Denmark

[21] Appl. No.: 346,781

[22] Filed: Nov. 30, 1994

[30] Foreign Application Priority Data

Nov. 30, 1993 [DK] Denmark ................... 1337/93

[51] Int. Cl.$^6$ .................... C07C 5/327; C07C 5/333
[52] U.S. Cl. ................... 585/658; 585/654; 585/656; 585/660
[58] Field of Search ................... 585/660, 658, 585/654, 656

[56] References Cited

U.S. PATENT DOCUMENTS

| | | |
|---|---|---|
| 3,855,330 | 12/1974 | Mendelsohn et al. |
| 4,418,237 | 11/1983 | Imai ................... 585/443 |
| 4,435,607 | 3/1984 | Imai . |
| 4,599,471 | 7/1986 | Ward . |
| 4,739,124 | 4/1988 | Ward . |

FOREIGN PATENT DOCUMENTS 0543535  5/1993  European Pat. Off. .

*Primary Examiner*—E. Rollins Cross
*Assistant Examiner*—E. D. Irzinski
*Attorney, Agent, or Firm*—Ostrolenk, Faber, Gerb & Soffen

[57] ABSTRACT

Process for the dehydrogenation of a hydrocarbon feed stream comprising steps of contacting the feed stream with a dehydrogenation catalyst in at least one dehydrogenation zone and reacting the feed stream to a hydrogen containing effluent stream;

admixing to the effluent stream an oxygen containing atmosphere in at least one mixing zone;

removing hydrogen from the effluent stream by reaction with oxygen in the oxygen containing atmosphere by contact with a hydrogen oxidation catalyst in at least one hydrogen removing zone, the improvement of which comprises employing massive forms of noble metals or alloys thereof as catalyst in the hydrogen removal zone.

4 Claims, No Drawings

PROCESS FOR THE DEHYDROGENATION OF HYDROCARBONS

BACKGROUND OF THE INVENTION

1. Field of the Invention

The present invention is directed to the preparation of mono-olefins by catalytic dehydrogenation of paraffinic hydrocarbons. In particular, the invention concerns certain improvements of industrial dehydrogenation processes for the preparation of mono-alkenes from corresponding alkanes having the same number of carbon atoms.

2. Description of the Related Art

The general reaction scheme in those processes can be expressed by the equilibrium reaction $$C_nH_{2n+2} \leftrightarrows C_nH_{2n} + H_2 \qquad (1),$$

which is thermodynamically unfavourable towards formation of alkenes. Because of the high energy required to cleave a C—H bond, the reaction takes place at high temperature with extensive thermocracking and combustion of hydrocarbon feed. To minimize formation of by-products at desired production rates, industrial dehydrogenation processes employ catalysts, which allow the above equilibrium reaction to proceed at lower temperatures. Catalysts, conventionally used in the processes, are supported platinum catalysts, or catalysts comprising chromic oxide impregnated on activated alumina and platinum-tin-zinc aluminate in the form of cylindrical or spherical pellets.

An essential process variable in the catalytic dehydrogenation process is pressure. Since the process is thermodynamically limited, reduced pressure results in increased equilibrium conversion. Thus, a higher alkene concentration can be obtained when removing gaseous hydrogen from the process gas leaving reaction (1).

Oxidative hydrogen removal from dehydrogenated or oxygenated hydrocarbon feed in presence of a catalyst or a hydrogen retention agent is known in the art.

Removal of hydrogen by contact with a dehydrogenation catalyst being capable of adsorbing hydrogen is mentioned in EP 543,535. At the disclosed process, the feed is contacted with the catalyst above 500° C. and hydrogen being formed during dehydrogenation is adsorbed on the catalyst. Catalysts, being able to adsorb hydrogen, are reducible metal oxides selected from Group IB, IIB and VIII of the Periodic Table. The hydrogen adsorbed on the catalyst is, subsequently, removed by applying heat, vacuum or by contact with an oxygen containing gas.

Dehydrogenation of hydrocarbons in separate beds of a dehydrogenation catalyst or in intermediate beds with a hydrogen selective oxidation catalyst is mentioned in U.S. Pat. No. 4,599,471 and U.S. Pat. No. 4,739,124. During the above processes, a dehydrogenated effluent stream from a bed of dehydrogenated catalyst is reheated and hydrogen is removed by passage through a subsequent bed of the hydrogen selective oxidation catalyst.

Use of alternating dehydrogenation and oxidation catalyst layers is further described in U.S. Pat. No. 3,855,330, U.S. Pat. No. 4,435,607 and U.S. Pat. No. 4,418,237. Formed hydrogen in the product gas is, thereby, removed by reaction with oxygen to steam in the presence of an oxidation catalyst.

In the known hydrogen removal processes, the employed catalysts are supported on highly porous inorganic support of alumina or ceria.

It has now been observed that catalyst activity and selectivity during catalytic hydrogen oxidation is limited by diffusion of reactants on the catalyst surface. Activity and selectivity of the catalysts are, thereby, strongly influenced by the number and size of surface pores. It has further been observed that even small changes in porosity of the catalyst surface result in considerable changes in activity and selectivity. Thereby, oxidation catalysts supported on highly porous support material show low selectivity at high temperatures.

In the dehydrogenation of alkanes, it is, however, required to carry out the process at high temperatures to provide practical dehydrogenation rates. At lower temperatures, the dehydrogenation equilibrium is, as mentioned before, unfavourable for the desired production of alkenes.

It has now been found that catalysts selected from the group of noble metals either in their pure metallic form or as alloys show improved catalytic activity and selectivity for the reaction of hydrogen with oxygen in a dehydrogenated carbonhydride process stream at high temperatures, when being used in their massive form.

Based on the above observations, it is believed that the low porosity of massive catalysts counteracts diffusion limitations and suppresses cracking and oxidation of carbonhydrates in such process gas.

SUMMARY OF THE INVENTION

Accordingly, a broad embodiment of the invention is directed toward a process for the dehydrogenation of a hydrocarbon feed stream comprising steps of contacting the feed stream with a dehydrogenation catalyst in at least one dehydrogenation zone and reacting the feed stream to a hydrogen containing effluent stream;

admixing to the effluent stream an oxygen containing atmosphere in at least one mixing zone;

removing hydrogen from the effluent stream by reaction with oxygen in the oxygen containing atmosphere by contact with a hydrogen oxidation catalyst in at least one hydrogen removing zone, the improvement of which comprises employing for the removal of hydrogen massive, i.e. unsupported forms of noble metals or alloys thereof as catalyst in the hydrogen removal zone.

The process will conveniently be carried out in a reactor containing two or more beds of the dehydrogenation catalyst with intermediate beds of the hydrogen removal catalyst. An oxygen containing atmosphere is admixed to the effluent stream after each dehydrogenation zone in a mixing zone on top of each hydrogen removal zone.

Introduction and admixing of oxygen containing atmosphere, which suitably is air or oxygen enriched air, may be performed through conventional gas distribution 10 aggregates mounted within the reactor on the top of the dehydrogenation zone.

A particular improvement is obtained when employing the massive catalysts in form of a wire screen gauze or other geometrical forms with an open body structure providing no additional pressure drop in the dehydrogenation reactor.

DETAILED DESCRIPTION OF THE PREFERRED EMBODIMENT

Example

Use of unsupported palladium and palladium-silver alloys as catalysts in the selective removal of hydrogen from a dehydrogenated process gas stream.

In the Example, palladium and palladium-silver alloy (70% Pd/30% Ag) catalysts in the form of flakes having a size of 16 sq. cm. per gram metal were used. 0.5 g of the catalyst was loaded in a quartz tubular reactor. Dehydrogenated feed gas was passed at a flow of 7 Nl/h and at a temperature of 500° C. through the reactor. The specific process conditions and results obtained thereby are summarized in the Table below.

In a comparison test, a palladium catalyst supported on alumina was tested at the same conditions as above. Results of the comparison test are also shown in the Table.

Oxidative Dehydrogenation Experiments in MPT-UNIT

| Effluent Gas, vol % | Feed Gas | Pd/Ag | Pd | Pd/Alumina |
|---|---|---|---|---|
| I-C4H10 | 71.3 | 73.08 | 74.57 | 73.03 |
| I-C4H8 | 9.3 | 10.10 | 9.73 | 9.24 |
| H2 | 7.3 | 5.00 | 4.36 | 5.78 |
| O2 | 2.5 | 0.00 | 0.00 | 0.00 |
| N2 | 9.6 | 10.34 | 10.31 | 10.01 |
| CO | 0 | 0.41 | 0.33 | 0.82 |
| CH4 | 0 | 0.33 | 0.19 | 0.31 |
| CO2 | 0 | 0.08 | 0.10 | 0.19 |
| C2H4 | 0 | 0.01 | 0.02 | 0.01 |
| C3H6 | 0 | 0.65 | 0.39 | 0.46 |
| Nl/H | 7.00 | 6.54 | 6.54 | 6.80 |
| % Conv. of O2 | | 100 | 100 | 100 |
| % Conv. of O2 | | 36 | 44 | 23 |
| % O2 to CO + CO2 | | 11 | 10 | 23 |
| % O to H2O | | 89 | 90 | 77 |
| % C to HC | | 0.67 | 0.41 | 0.52 |
| % C to CO + CO2 | | 0.14 | 0.12 | 0.30 |
| % C loss | | 0.81 | 0.53 | 0.82 |

As apparent from the above results, oxidation of hydrogen proceeds at a higher rate in contact with a massive catalyst, than in presence of the supported palladium catalyst. The average conversion rate of $H_2$ is 40% with the unsupported catalyst, which is nearly twice as high as by use of the supported catalyst. Furthermore, oxygen reacts more selectively with hydrogen over the massive catalysts, which is obvious from the low per cent conversion of $O_2$ to $CO+CO_2$ and %C to $CO+CO_2$ in the Table.

What is claimed is:

1. In a process for the dehydrogenation of a hydrocarbon feed stream comprising the steps of:

contacting the feed stream with a dehydrogenation catalyst in at least one dehydrogenation zone and reacting the feed stream to produce a hydrogen-containing effluent stream;

admixing to the effluent stream an oxygen-containing atmosphere in at least one mixing zone;

removing hydrogen from the effluent stream by reaction with oxygen in the oxygen-containing atmosphere by contact with a hydrogen oxidation catalyst in at least one hydrogen removal zone, the improvement of which comprises employing unsupported forms of noble metals or alloys thereof as catalyst in the at least one hydrogen removal zone.

2. Process of claim 1, wherein the catalyst is a massive form of palladium or palladium-silver alloy.

3. Process of claim 1, wherein the catalyst is in the form of a wire mesh gauze.

4. Process of claim 1, wherein the catalyst is in the form of flakes.

* * * * *

UNITED STATES PATENT AND TRADEMARK OFFICE
CERTIFICATE OF CORRECTION

PATENT NO. : 5,498,816
DATED      : March 12, 1996
INVENTOR(S): Nielsen et al.

It is certified that error appears in the above-indentified patent and that said Letters Patent is hereby corrected as shown below:

Col. 3, line 30, please correct line 13 of the table as follows:

```
Change "% Conv.  of 02    36    44    23" to
       --% Conv. H2       36    44    23--.
```

Signed and Sealed this

Ninth Day of July, 1996

BRUCE LEHMAN

*Attest:*

*Attesting Officer*    *Commissioner of Patents and Trademarks*